United States Patent
Moriya et al.

(10) Patent No.: US 8,243,265 B2
(45) Date of Patent: Aug. 14, 2012

(54) METHOD AND APPARATUS FOR DETECTING FOREIGN MATERIALS AND STORAGE MEDIUM

(75) Inventors: Tsuyoshi Moriya, Tokyo (JP); Hiroshi Nagaike, Nirasaki (JP); Hideaki Yakushiji, Nirasaki (JP)

(73) Assignee: Tokyo Electron Limited, Tokyo (JP)

( * ) Notice: Subject to any disclaimer, the term of this patent is extended or adjusted under 35 U.S.C. 154(b) by 378 days.

(21) Appl. No.: 12/617,235

(22) Filed: Nov. 12, 2009

(65) Prior Publication Data
US 2010/0118302 A1 May 13, 2010

(30) Foreign Application Priority Data

Nov. 13, 2008 (JP) ................................. 2008-291375

(51) Int. Cl.
*G01N 21/00* (2006.01)
(52) U.S. Cl. .................................................. 356/237.5
(58) Field of Classification Search ................ 356/237.5
See application file for complete search history.

(56) References Cited

U.S. PATENT DOCUMENTS

| 5,534,309 | A | * | 7/1996 | Liu | 427/458 |
| 5,893,271 | A | * | 4/1999 | Brink | 62/93 |
| 7,239,381 | B2 | * | 7/2007 | Gilton | 356/237.2 |
| 7,317,521 | B2 | * | 1/2008 | Gilton | 356/237.2 |
| 2005/0062959 | A1 | * | 3/2005 | Gilton | 356/237.2 |
| 2006/0203234 | A1 | * | 9/2006 | Gilton | 356/237.2 |
| 2007/0209591 | A1 | | 9/2007 | Nagaike et al. | |

FOREIGN PATENT DOCUMENTS

| JP | 2007-273947 | | 10/2007 |
| JP | 2007273947 | A * | 10/2007 |
| KR | 10-2001-0021675 | A | 3/2001 |

OTHER PUBLICATIONS

Korean Office Action issued on Apr. 25, 2011 in corresponding Korean Application No. 10-2009-0109931 (with an English Translation).

* cited by examiner

*Primary Examiner* — Roy M Punnoose
(74) *Attorney, Agent, or Firm* — Oblon, Spivak, McClelland, Maier & Neustadt, L.L.P.

(57) ABSTRACT

A foreign material detecting method for detecting a foreign material attached to a substrate surface includes a spraying step of spraying an organic solvent or an oil-phase material containing a halogen element to the substrate surface, a condensing step of emphasizing the foreign material by condensing the sprayed organic solvent or oil-phase material around the foreign material attached to the substrate surface by controlling a temperature of the substrate surface, and a surface inspecting step of detecting the foreign material emphasized by the condensation of the organic solvent or the oil-phase material by a surface inspecting device.

9 Claims, 4 Drawing Sheets

METHOD AND APPARATUS FOR DETECTING FOREIGN MATERIALS AND STORAGE MEDIUM

FIELD OF THE INVENTION

The present invention relates to a method and an apparatus for detecting foreign materials and a storage medium; and, more particularly, to a method for detecting foreign materials such as polymers or the like attached to a substrate surface by emphasizing the foreign materials through a pre-process and inspecting the substrate surface.

BACKGROUND OF THE INVENTION

The attachment of particles onto a surface of a semiconductor substrate (hereinafter, referred to as "wafer") is one of the reasons for deteriorating a production yield in a semiconductor manufacturing process. The particles are foreign materials to an integrated circuit, making the quality thereof unacceptable. Conventionally, a particle size that deteriorates the production yield is, e.g., about 50 nm to 70 nm, and can be detected by a surface inspection device such as a Surfscan or the like.

Recently, a trend towards high integration of chips is accelerated in a semiconductor industry, and this leads to a demand for a line width of an integrated circuit which is smaller than or equal to, e.g., about 50 nm. Therefore, a particle size that affects an integrated circuit becomes smaller, and it is expected that the particle size affecting the integrated circuit becomes about 20 nm or less in a near future.

A detection limit of a fine particle measuring device as a present surface inspection device is, e.g., about 40 nm. Therefore, it is expected that it will be difficult to detect particles as foreign materials attached onto a wafer surface in the near future. In that case, it is not possible to manage the condition in an accommodation chamber of a substrate processing apparatus for performing a predetermined process on a substrate such as a wafer or the like, so that a yield of product substrates deteriorates.

To that end, there is suggested in, e.g., Japanese Patent Laid-open Publication No. 2007-273947, a substrate surface inspecting method for detecting even fine particles, which may cause problem in the future, by using the present surface inspection device.

Japanese Patent Laid-open Publication No. 2007-273947 discloses a method for indirectly detecting particles on a substrate surface. In this method, water in the atmosphere surrounding a wafer onto which particles having a diameter of about 30 µm are attached is put into a supercooled state by supercooling the wafer to a temperature lower than or equal to, e.g., about −20° C. Next, the supercooled water is attached around the particles on the surface of the wafer. Thereafter, the collected supercooled water is released from the supercooled state and thus freezes, so that the frozen water grows in an ice crystal having the particle as a core and the ice crystal is detected.

In the prior art, however, the ice crystal is not always stable. Thus, when the substrate on which the particles are emphasized by the ice crystal attached thereto is transferred from a surface processing apparatus as a pre-processing apparatus to a surface inspection device for detecting particles, the ice crystal is molten to be removed. In order to protect the snow crystal-shaped frozen water, it is considered to spray, e.g., cyanoacrylate thereto. However, a reaction product of cyanoacrylate and water (snow crystal) is stable and thus cannot be decomposed. Accordingly, the substrate that has been subjected to the surface inspection cannot be restored to the original state, which prevents the inspected substrate from being subjected to another inspection or from being used as a product.

SUMMARY OF THE INVENTION

In view of the above, the present invention provides a method and an apparatus for detecting foreign materials attached onto a substrate surface, which can stably and accurately detect even fine foreign materials smaller than a detection limit of a conventional measuring device and can be widely used and suitable for inspection of mass-produced substrates, and a storage medium.

In accordance with a first aspect of the present invention, there is provided a foreign material detecting method for detecting a foreign material attached to a substrate surface, the method including: a spraying step of spraying an organic solvent or an oil-phase material containing a halogen element to the substrate surface; a condensing step of emphasizing the foreign material by condensing the sprayed organic solvent or oil-phase material around the foreign material attached to the substrate surface by controlling a temperature of the substrate surface; and a surface inspecting step of detecting the foreign material emphasized by the condensation of the organic solvent or the oil-phase material by a surface inspecting device.

In accordance with a second aspect of the invention, there is provided a foreign material detecting apparatus for detecting a foreign material attached to a surface of a substrate, the apparatus including: a surface processing device having an accommodation chamber for accommodating the substrate, for preprocessing the surface of the substrate; and a surface inspecting device for inspecting the preprocessed surface of the substrate, wherein the surface processing device includes: a spraying unit for spraying an organic solvent or an oil-phase material containing a halogen element to the surface of the substrate; and a temperature control unit for condensing the sprayed organic solvent or oil-phase material around the foreign material attached to the surface of the substrate by controlling a temperature of the surface of the substrate, and wherein the surface inspecting device includes: a surface inspecting unit for inspecting the surface of the substrate; and a heating unit for heating the foreign material on the substrate.

In accordance with a third aspect of the invention, there is provided a computer readable storage medium storing therein a program for causing a computer to perform a foreign material detecting method for detecting a foreign material attached to a surface of a substrate, wherein the foreign material detecting method includes: a spraying step of spraying an organic solvent or an oil-phase material containing a halogen element to the substrate surface; a condensing step of emphasizing the foreign material by condensing the sprayed organic solvent or oil-phase material around the foreign material attached to the substrate surface by controlling a temperature of the substrate surface; and a surface inspecting step of detecting the foreign material emphasized by the condensation of the organic solvent or the oil-phase material by a surface inspecting device.

BRIEF DESCRIPTION OF THE DRAWINGS

The other objects and features of the present invention will become apparent from the following description of embodiments, given in conjunction with the accompanying drawings, in which.

DETAILED DESCRIPTION OF THE EMBODIMENT

The present inventors have performed various examinations on a method for detecting particles as foreign materials attached to a substrate surface and have found that if the particles are enlarged or emphasized, they can be detected by a conventional measuring device, e.g., an optical microscope, an electron microscope, a laser light scattering method or the like. Based on the above, the present inventors have researched a method for enlarging or emphasizing particles attached to a substrate surface and a method for detecting the particles. As a result, the present inventors have found that the particles are emphasized by spraying an organic solvent or an oil-phase material containing a halogen element onto the substrate surface and condensing the sprayed organic solvent or oil-phase material around the particles by controlling a temperature of the substrate surface to a predetermined temperature.

In other words, the foreign material detecting method of the present invention includes a spraying step of spraying an organic solvent or an oil-phase material containing a halogen element onto the substrate surface and a condensing step for emphasizing the foreign materials by condensing the sprayed organic solvent or oil-phase material around the foreign material attached to the substrate surface by controlling a temperature of substrate surface.

The embodiments of the present invention will be described with reference to the accompanying drawings which form a part hereof.

The following is description of a substrate processing system including a foreign material detecting apparatus of the present invention which is used to perform the foreign material detecting method of the present invention.

Figure 1:
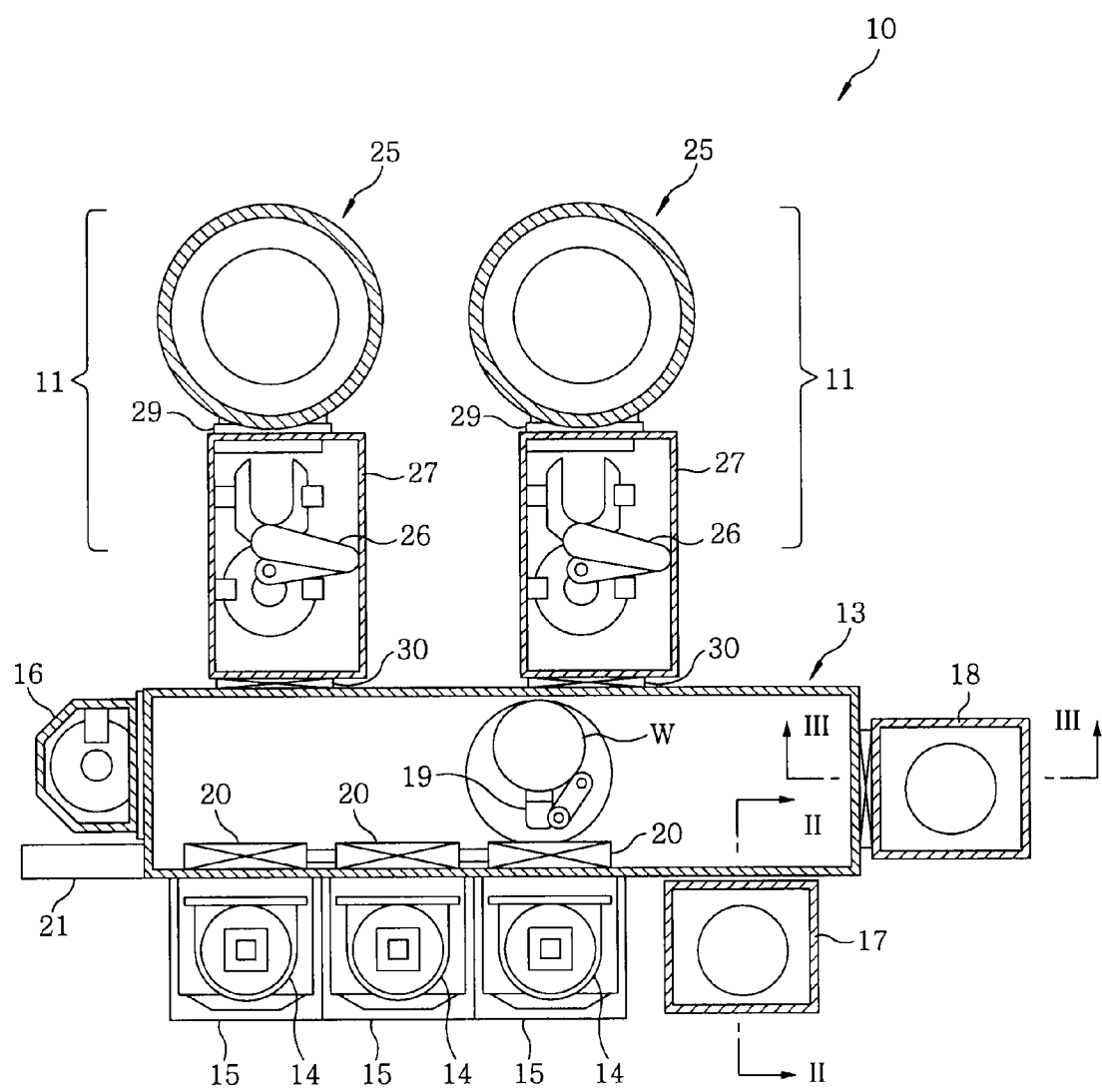
FIG. 1 is a top view showing a schematic configuration of a substrate processing system including an apparatus for detecting foreign materials in accordance with the present invention.

FIG. 1 is a top view showing a schematic configuration of the substrate processing system including the foreign material detecting apparatus of the present invention.

Referring to FIG. 1, a substrate processing system 10 mainly includes two process ships 11 for performing a reactive ion etching (RIE) process or the like on a wafer W for semiconductor devices, a rectangular shaped loader module 13 serving as a common transfer chamber to which the two process ships 11 are connected, a surface processing device 17 connected to the loader module 13, and a surface inspecting device 18 connected to the loader module 13.

The loader module 13 is connected to three FOUP (Front Opening Unified Pod) mounting tables 15, each for mounting thereon a FOUP 14 serving as a container for accommodating, e.g., twenty-five wafers W, and an orienter 16 for performing pre-alignment of the wafer W unloaded from the FOUP 14. Further, the surface processing device 17 and the surface inspecting device 18 function as a foreign material detecting apparatus.

The two process ships 11 are connected to one of long sidewalls of the loader module 13, and are disposed opposite to the three FOUP mounting tables 15 connected to the other long sidewall of the loader module 13. The orienter 16 is coupled to one of short sidewalls of the loader module 13, and the surface inspecting device 18 is coupled to the other short sidewall of the loader module 13. The surface processing device 17 is disposed on the long sidewall of the loader module 13 in parallel with the three FOUP mounting tables 15.

The loader module 13 includes a scalar dual-arm type transfer arm unit 19 for transferring the wafer W disposed therein; and three loading ports 20, serving as input ports of the wafer W, disposed on the sidewall corresponding to the respective FOUP mounting tables 15. The transfer arm unit 19 takes out the wafer W from the FOUP 14 mounted on the FOUP mounting table 15 via the loading port 20 and transfers the taken wafer W between the loader module 13 and the process ship 11, the orienter 16, the surface processing device 17 or the surface inspecting device 18.

The process ship 11 includes a process module 25 as a plasma processing chamber for performing an RIE process on the wafer W, and a load-lock module 27 having a link-shaped single pick type transfer arm 26 for transferring the wafer W to the process module 25.

An inner pressure of the loader module 13 is maintained at an atmospheric pressure, whereas an inner pressure of the process module 25 is kept at a vacuum. Accordingly, the load-lock module 27 of the process ship 11 includes a vacuum gate valve 29 provided at a connection portion with the process module 25 and an atmospheric gate valve 30 provided at a connection portion with the loader module 13 so that the load-lock module 27 of the process ship 11 is configured as a vacuum preliminary transfer chamber whose inner pressure can be controlled.

The substrate processing system 10 includes a system controller (not shown) for controlling the operations of the process ships 11 having the process module 25 and the load-lock module 27, the loader module 13, the orienter 16, and the foreign material detecting system, for detecting foreign materials attached to the peripheral end portion of the substrate, having the surface processing device 17 and the surface inspecting device 18; and an operation panel 21 disposed at one end in the longitudinal direction of the loader module 13.

The system controller controls an operation of each component based on a recipe as a program corresponding to an RIE process. The operation panel 21 has a display unit (not shown) formed of, e.g., LCD (Liquid Crystal Display), and the display unit displays an operation state of each component.

Figure 2:
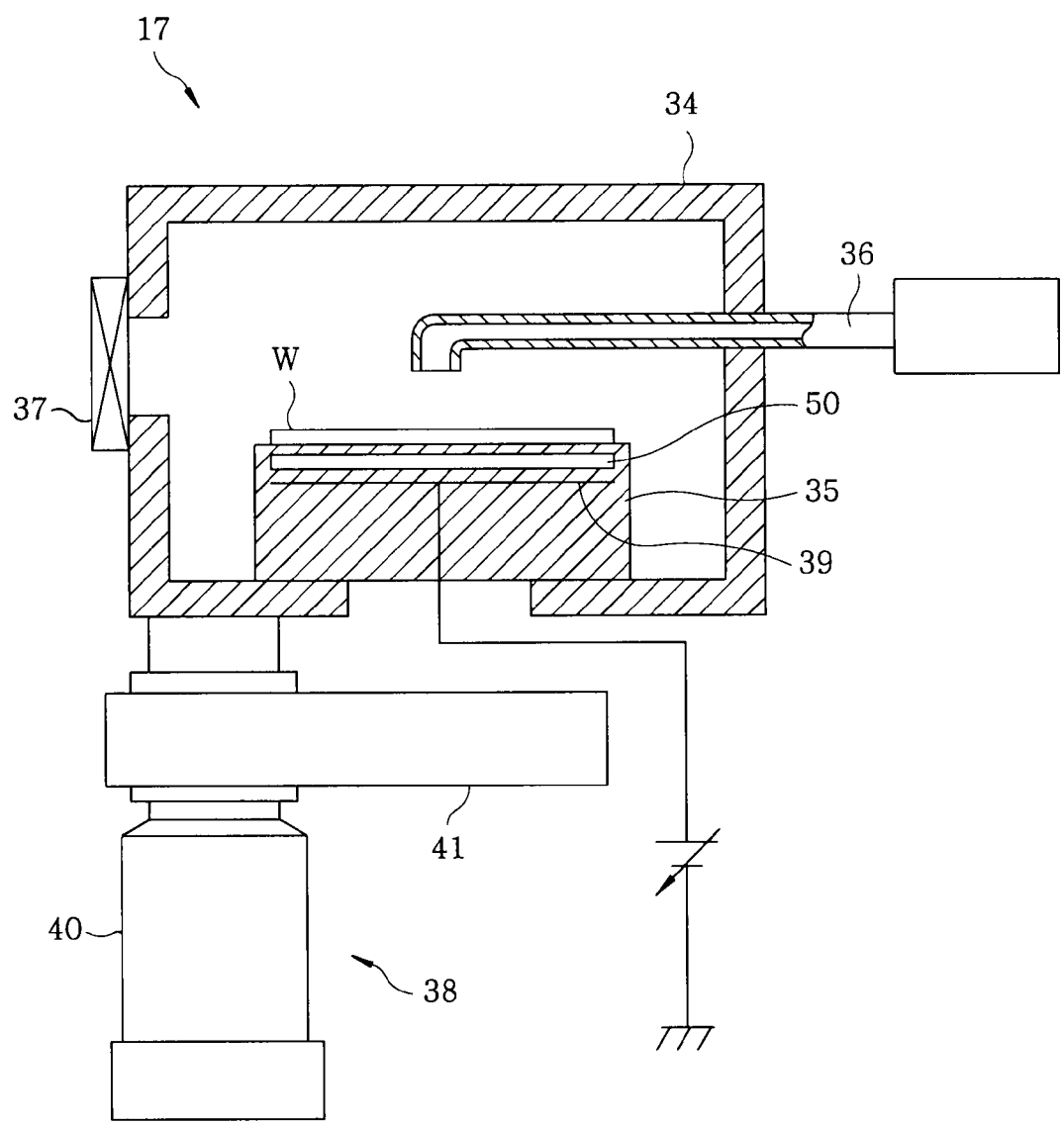
FIG. 2 describes a cross sectional view taken along line II-II of FIG. 1.

FIG. 2 illustrates a cross sectional view taken along line II-II of FIG. 1. For convenience of description, an upper side in FIG. 2 will be referred to as "upper (side), and a lower side in FIG. 2 is referred to as "lower (side)".

Referring to FIG. 2, the surface processing device 17 includes a housing-shaped accommodation chamber 34; a wafer stage 35 provided at a lower portion in the accommodation chamber 34, for mounting thereon the wafer W; a spraying unit 36 for spraying an inspection agent to be described later; an openable/closable gate valve 37 disposed on a side surface of the accommodation chamber 34; and a gas exhaust unit 38 for exhausting fluid in the accommodation chamber 34. The surface processing device 17 is connected to the loader module 13 via the gate valve 37. The interior of the accommodation chamber 34 communicates with the interior of the loader module 13 by opening the gate valve 37.

The wafer stage 35 has therein a heat transfer heater 39 disposed below the mounting surface of the wafer W, and the wafer W mounted on the wafer stage 35 is heated to a desired temperature. Further, the wafer stage 35 has therein, e.g., a peltier element 50, as a cooling unit for cooling the wafer W, so that the wafer W mounted on the wafer stage 35 is cooled to a desired temperature by the peltier element 50. The peltier element is an electronic component, and is a plate-shaped semiconductor device using the Peltier effect, i.e., the phenomenon in which, when current is applied to the junction of two types of metals, heat is transferred from one of the metals to the other metal. If current is applied to the junction of two types of metals, one surface absorbs the heat and the other surface emits the heat. The heat absorbing surface is a cooling surface, and the heat emitting surface is a heating surface. When the polarity of current is reversed, the cooling surface and the heating surface are switched, and high-accuracy temperature control can be carried out. In this embodiment, the wafer stage 35 cools the wafer W by the peltier element 50, and heats the wafer W by the heat transfer heater 39. However, the wafer W may be cooled and heated by the peltier element 50.

The spraying unit 36 sprays an inspection agent to be described later to the surface of the wafer W. The gas exhaust unit 38 includes a TMP (Turbo Molecular Pump) 40 for exhausting gas or the like in the accommodation chamber 34, a DP (Dry Pump) (not shown) provided at an exhaust side of the TMP 40, and a pressure control valve 41 disposed between the accommodation chamber 34 and the TMP 40. The pressure control valve 41 sets an inner pressure of the accommodation chamber 34 to a desired pressure.

The surface processing device 17 performs an inspection pretreatment to be described later on the wafer W as a surface inspection target which is loaded into the surface inspecting device 18.

Figure 3:
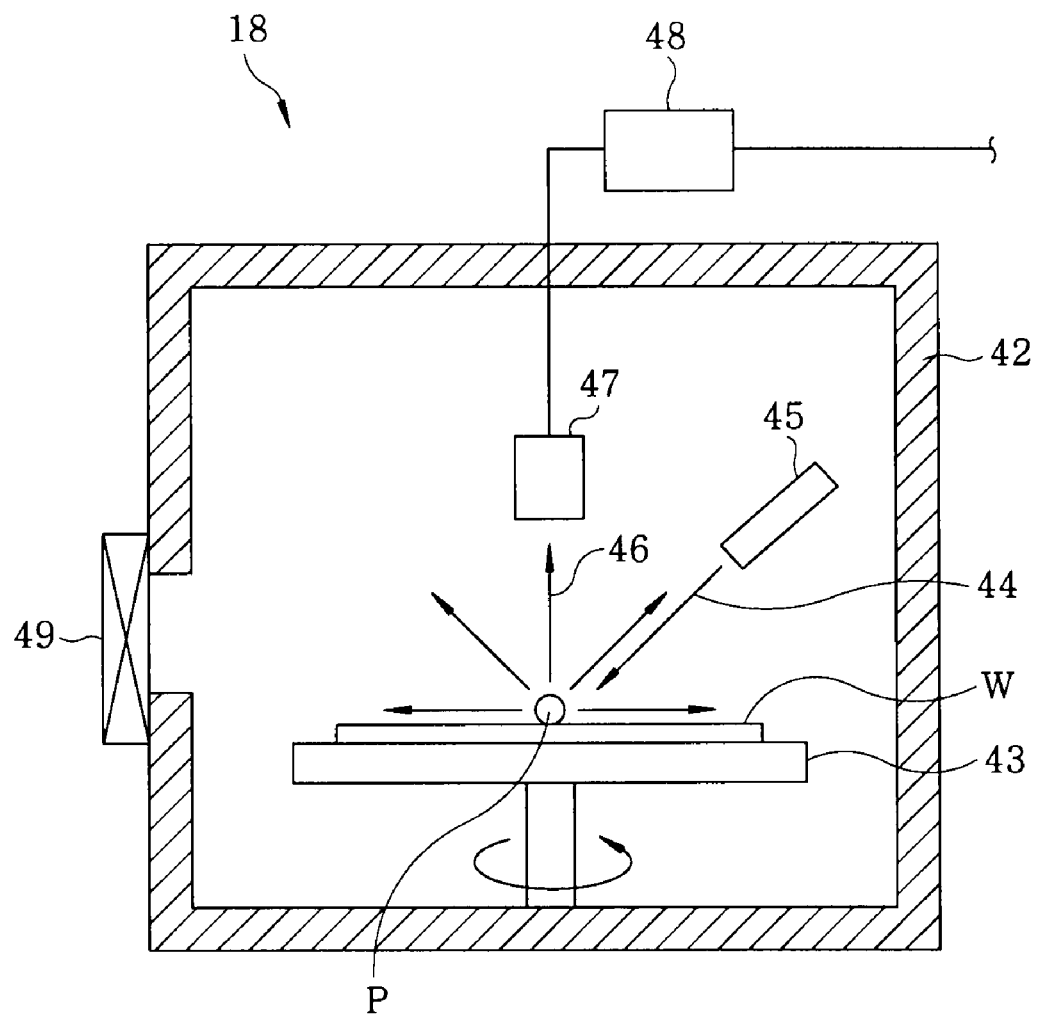
FIG. 3 depicts a cross sectional view taken along line III-III of FIG. 1.

FIG. 3 is a cross sectional view taken along line III-III of FIG. 1. For convenience of description, an upper side in FIG. 3 will be referred to as "upper (side), and a lower side in FIG. 3 is referred to as "lower (side)".

Referring to FIG. 3, the surface inspecting device 18 includes a housing-shaped accommodation chamber 42; a wafer stage (mounting table) 43 provided at a lower portion in the accommodation chamber 42, for mounting thereon and rotating the wafer W; a laser beam irradiating unit 45 for irradiating a laser beam 44 to the surface of the rotating wafer W; a light receiving unit (collimator) for receiving a part of scattered light generated by irradiating the laser beam 44 to the particles P attached to the substrate surface; a photoelectric conversion unit (photo multiplier) 48 for converting the scattered light received by the light receiving unit 47 into an electrical signal; and an openable/closable gate valve 49 disposed on a side surface of the accommodation chamber 42. The photoelectric conversion unit 48 is connected to the system controller (not shown).

The surface inspecting device 18 is connected to the loader module 13 via the gate valve 49 (see FIG. 1). The interior of the accommodation chamber 42 communicates with the interior of the loader module 13 by opening the gate valve 49.

In the surface inspecting device 18 configured as described above, if a particle P is attached to the surface of the wafer W mounted on the wafer stage 43, the irradiation of the laser beam 44 to the particle P leads to generation of scattered light 46. A part of the scattered light 46 is received by the light receiving unit 47, and converted into an electrical signal by the photoelectric conversion unit 48. The electrical signal thus obtained is transmitted to the system controller. The intensity of the scattered light 46 varies in accordance with the size of the particle P. Thus, the system controls detects the existence/non-existence and the size of the particle P based on the voltage of the electrical signal which corresponds to the intensity of the scattered light 46.

The following is description of a foreign material detecting method using a foreign material detecting apparatus in accordance with the present invention.

In the foreign material detecting method of the present invention, the particles P attached to the surface of the wafer W as an inspection target object are apparently enlarged by condensing an organic solvent or an oil-phase material containing a halogen element around the particles P and then solidifying the condensate (hereinafter, referred to as "inspection agent") in a flower shape. Accordingly, the particles P can be indirectly detected by using a conventional measuring device.

Hereinafter, the foreign material detecting method in accordance with an embodiment of the present invention will be described in detail with reference to the drawings.

FIGS. 4A to 4F are schematic views illustrating steps of processing a substrate surface and steps of inspecting the processed surface.

In this embodiment, the particle P attached to the substrate surface is detected as will be described below.

Figure 4A:
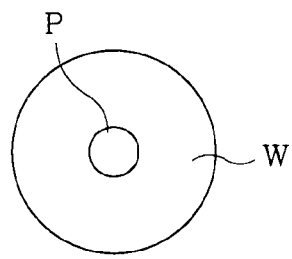
FIGS. 4A to 4F offer schematic views illustrating steps for processing a surface of a substrate and steps for inspecting the processed surface.
Figure 4B:
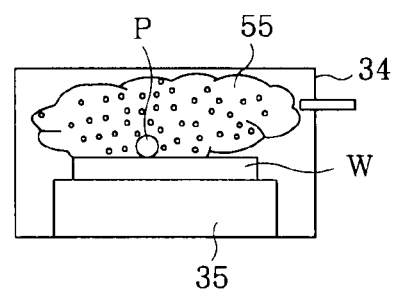
Figure 4C:
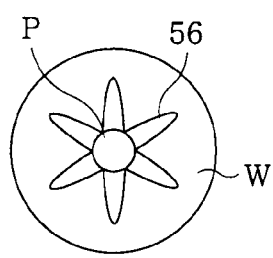

First of all, there is prepared a wafer W as an inspection target object onto which the particle P as foreign material is attached (FIG. 4A).

Next, the wafer W to which the particle P is attached is loaded into the accommodation chamber 34 of the surface processing device 17 (see FIG. 2) by the transfer arm unit 19 (see FIG. 1), and is mounted on the wafer stage 35. Then, an inner pressure of the accommodation chamber 34 is depressurized to a medium vacuum state or a low vacuum state of, e.g., about 133 Pa to 13 kPa (about 1 to 100 Torr), by the pressure control valve 41. An organic solvent or an oil-phase material containing a halogen element is sprayed as a gas-phase material onto the surface of the wafer W under the medium vacuum state or a low vacuum state and attached thereto (FIG. 4B) (spraying step). As for the inspection agent 55, it is preferable to use, e.g., perfluoropolyether oil (e.g., DEMNUM (trademark) made by Daikin Industries LTD.).

After the inspection agent 55 in a gas phase is sprayed and attached onto the surface of the wafer W, the surface temperature of the wafer W is cooled to about 0° C. to about 30° C. by the heat transfer heater 39 or the peltier element 50 built in the wafer stage 35. Accordingly, the inspection agent sprayed to the surface of the wafer W is condensed, thereby forming a flower-shaped mark (condensate) 56 around the particle P (FIG. 4C) (condensing step). The particle P is apparently enlarged and emphasized by the condensate 56. The flower-shaped condensate 56 formed by the condensation of the inspection agent is stable and thus maintained in a solid state in the atmosphere.

Figure 4D:
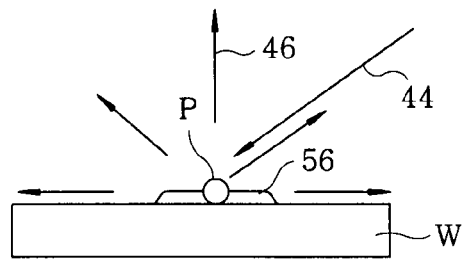

Next, the wafer W onto which the particle P emphasized by the condensate 56 is attached is unloaded from the surface processing device 17. The wafer W is loaded into the accommodation chamber 42 of the surface inspecting device 18 and mounted on the wafer stage 43. Thereafter, the laser beam 44 is irradiated to the surface of the wafer W by the laser beam irradiating unit 45 while rotating the wafer stage 43. At this time, since the condensate 56 of the inspection agent is formed around the particle P on the surface of the wafer W while using the particle P as a core, the laser beam 44 is further scattered by the condensate 56 that has apparently enlarged the particle P, thus generating the scattered light 46 (FIG. 4D). Accordingly, the amount of the scattered light 46 received by the light receiving unit 47 increases considerably compared to the case where only the particle P exists and, also, the voltage of the electrical signal converted by the photoelectric conversion unit 48 increases. As a consequence, the particle P on the surface of the wafer W is detected reliably (surface inspecting step).

Figure 4E:
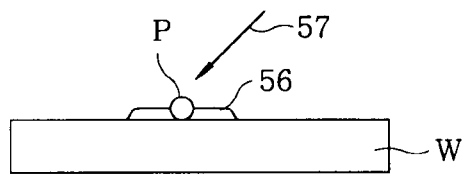
Figure 4F:
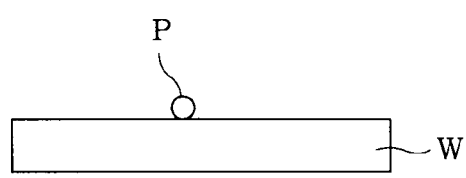

The particle P detected on the wafer W is heated to, e.g., about 30° C. to about 130° C., by irradiating an electron beam 57 from an electron beam irradiation unit (not shown) to the particle P attached onto the surface of the wafer W (FIG. 4E). At this time, the simultaneously heated condensate 56 of the inspection agent is scattered and removed, so that the wafer W is restored to the state before the inspection in which only the particle P is attached (FIG. 4F) (restoring step).

In accordance with this embodiment, the particle P can be apparently enlarged by solidifying the condensate 56 of the inspection agent 55 while using the particle P as a core. Therefore, even fine particles P can be indirectly detected by using a conventional surface inspecting device, e.g., a Surfscan or the like. Accordingly, it is possible to monitor the generation state of the particle P in the substrate processing apparatus for processing the wafer W, and also possible to prevent the deterioration of the yield by managing the condition of the process chamber.

Moreover, the foreign material detecting method of this embodiment can quickly detect the particle P attached to the surface of the wafer W by using a conventional surface inspecting device. For that reason, this foreign material detecting method can be widely used and is suitable for inspection of mass-produced substrates.

Further, in accordance with this embodiment, after the particle P attached to the surface of the wafer W is detected, the condensate 56 of the inspection agent 55 is scattered and removed by heating. Accordingly, the wafer W can be restored to the state before the inspection. Thus, the particle can be subjected to another inspection, and even the inspected wafer W can maintain its value as a product. In the prior art, the apparently enlarged foreign material (particle P) is protected by spraying cyanoacrylate thereonto, so that the inspected wafer W cannot be restored to the original state. However, in this embodiment, the inspected wafer W can easily be restored to the state before the inspection as described above and, hence, the yield does not deteriorate.

In this embodiment, the condensate 56 solidified while using the particle P as a core is stable in the atmosphere. Therefore, the surface inspection may not be carried out immediately upon completion of the surface processing in which the condensate 56 is formed around the particle P. Further, the surface processing and the surface inspecting can be performed at any arbitrary time and the places at which the surface processing and the surface inspecting are performed can be changed arbitrarily.

In this embodiment, the organic solvent or the oil-phase material containing a halogen element which is used as an inspection agent preferably has low viscosity and high volatility. When an inspection agent having low volatility is used, it is preferable to dissolve or disperse the inspection agent in alcohol or water and then spray the aerosolized inspection agent to the surface of the wafer W. In this way, the inspection agent can be easily sprayed, and effectively distributed and attached to the surface of the wafer W.

As for the inspection agent, there is used an organic solvent or an oil-phase material containing at least one of F, Cl and Br. Specifically, an oil-phase material mainly including perfluoropolyether oil (e.g., DEMNUM (trademark) made by Daikin Industries LTD.) is used in this embodiment, it is also possible to use Fomblin, Krytox or the like.

The reason that an organic solvent or an oil-phase material containing a halogen element is preferably used as an inspection is not clear. However, it is considered that, due to including CF, CO and CH bonds, the condensate 56 can be stably formed in the atmosphere and can be easily removed by heating.

In this embodiment, when an inspection agent or a dispersion solution in which the inspection agent is dispersed in alcohol or water is sprayed to the surface of the wafer W, it is preferable to employ an electrostatic spraying method. In this case, dispersed liquid droplets have a stable size in the unit of, e.g., nm, and thus can be uniformly dispersed.

In this embodiment, the inspection agent may be sprayed onto the wafer W under the atmospheric pressure. However, it is preferable to spray the inspection agent under the depressurized atmosphere. This facilitates the evaporation of liquid components in the inspection agent sprayed to the surface of the wafer W or the evaporation of solvent components in the solution in which the inspection agent is dissolved or dispersed in alcohol or water. As a consequence, the condensate 56 can be easily solidified.

In this embodiment, after the inspection agent is sprayed, the wafer W is cooled by the peltier element 60 built in the wafer stage 35. However, the wafer W may be cooled by depressurizing the accommodation chamber 34. In that case, the depressurized atmosphere set during the spraying of the inspection agent can be used for cooling of the wafer W.

In this embodiment in which an organic solvent or an oil-phase material is used as the inspection agent, the condensate 56 solidified while using the particle P as a core may not be necessarily formed in a flower shape. It is sufficient that the particle P is apparently enlarged enough to be detected.

In the restoring step of this embodiment, the heating may be performed simply by the heat transfer heater depending on a configuration of the apparatus or the like without irradiating an electron beam. In that case as well, the wafer W can be restored to the original state by removing the condensate 56. However, the case of irradiating an electron beam is preferable because only the particle P can be heated in a pinpoint manner without heating unnecessary portions. Moreover, a laser beam used for the detection of the particle P by the surface inspecting device 18 has a short wavelength close to, e.g., However, as for an electron beam for scattering and removing the condensate 56 of the inspection agent 55, there is used a beam having a long wavelength greater than or equal to, e.g., about 1 μm. Besides, the condensate 56 of the inspection agent can be simply removed by a general cleaning operation as well as by the heating operation.

In this embodiment, the surface inspecting device employing the laser beam scattering method is used as an apparatus for measuring the particle P emphasized by the condensate 56 of the inspection agent. However, it is also possible to use, e.g., an optical microscope, an electron microscope or the like, without being limited thereto.

In the above-described embodiment, the substrate processing system includes the surface processing device 17 and the surface inspecting device 18. However, the surface processing device 17 and/or the surface inspecting device 18 may be separately provided from the substrate processing system. Further, the separately provided surface inspecting device may include the components of the surface processing device. Moreover, the surface processing device 17 and the surface inspecting device 18 may be integrated in a single unit.

In the substrate processing system of the above-described embodiment, a substrate subjected to surface inspection is not limited to a wafer for semiconductor devices, and may be various substrates for use in an LCD (Liquid Crystal Display), an FPD (Flat Panel Display) and the like, a photo mask, a CD substrate, a printed circuit board or the like.

It is to be understood that the object of the present invention can also be attained by supplying to a system or an apparatus a storage medium storing a program codes of software that realize the functions of the aforementioned embodiments, and then causing a computer (CPU or MPU, etc.) of the apparatus or the system to read out and execute the program codes stored in the storage medium.

In this case, the program codes themselves read out from the storage medium realize the functions of the aforementioned embodiments and, hence, the program codes and the storage medium storing the program codes constitute the present invention.

The storage medium storing the program codes may be, e.g., a floppy (registered trademark) disk, a hard disk, a magnetic-optical disk, an optical disk such as a CD-ROM, a CD-R, a CD-RW, a DVD-ROM, a DVD-RAM, a DVD-RW, a DVD+RW or the like, a magnetic tape, a non-volatile memory card, a ROM or the like. Alternatively, the program codes may be downloaded via a network.

Besides, it is to be understood that the functions of the aforementioned embodiments may be accomplished not only by executing the program codes read out by the computer, but also by causing an OS (operating system) or the like that operates on the computer to perform a part or all of the actual operations based on instructions of the program codes.

Furthermore, it is to be understood that the functions of the aforementioned embodiments may also be accomplished by writing the program code read out from the storage medium on a memory provided on a function expansion board inserted into the computer or in a function expansion unit connected to the computer, and then causing the CPU or the like provided on the expansion board or in the expansion unit to perform a part or all of the actual operations based on instructions of the program codes.

According to the embodiments of the present invention, the foreign material attached to the surface of the substrate can be apparently enlarged by the condensate. Thus, the foreign materials attached to the surface of the substrate can be detected accurately.

Further, the substrate that has been used for the detection of foreign material can maintain its value as a product. As a consequence, the deterioration of the yield can be prevented.

Further, the organic solvent or the oil-phase material condensed around the foreign materials can be effectively scattered by heating the foreign material on the substrate surface in a pinpoint manner.

Further, since the organic solvent or the oil-phase material containing a halogen element is dissolved or dispersed in alcohol or water and sprayed to the surface of the substrate, it is possible to use an organic solvent or an oil-phase material having high viscosity and low volatility.

Further, the foreign material can be apparently enlarged by condensing the organic solvent or the oil-phase material sprayed onto the substrate surface.

Further, liquid components in the sprayed organic solvent or oil-phase material are easily scattered and the condensation of the organic solvent or the oil-phase material can be facilitated.

Further, since the halogen element is water-soluble, the organic solvent or the oil-phase material is mixed with water and can be easily sprayed. After the spraying operation, the condensate formed around the foreign materials can be easily removed by the heating. Therefore, the substrate that has been subjected to the detection of foreign materials can be restored to the original state.

Further, the condensate formed around the foreign materials can be extremely easily removed by the heating. Accordingly, the substrate that has been subjected to the detection of foreign materials can be easily restored to the original state.

Further, the foreign material detecting apparatus can stably and accurately detect even fine foreign materials smaller than or equal to a detection limit of a conventional measuring device. For that reason, the foreign material detecting apparatus can be widely used and is suitable for inspection of mass-produced substrates.

While the invention has been shown and described with respect to the embodiments, it will be understood by those skilled in the art that various changes and modification may be made without departing from the scope of the invention as defined in the following claims.

What is claimed is:

1. A foreign material detecting method for detecting a foreign material attached to a substrate surface, the method comprising:
   a spraying step of spraying an organic solvent or an oil-phase material containing a halogen element to the substrate surface;
   a condensing step of emphasizing the foreign material by condensing the sprayed organic solvent or oil-phase material around the foreign material attached to the substrate surface by controlling a temperature of the substrate surface;
   a surface inspecting step of detecting the foreign material emphasized by the condensation of the organic solvent or the oil-phase material by a surface inspecting device; and
   a restoring step of scattering the condensed organic solvent or the condensed oil-phase material by heating the substrate surface after the surface inspecting step,
   wherein in the restoring step, the substrate is restored such that only the foreign material is attached thereon while the condensed organic solvent or the condensed oil-phase material is removed.

2. The foreign material detecting method of claim 1, wherein the restoring step is performed by irradiating, with an electron beam, the foreign material attached to the substrate surface.

3. The foreign material detecting method of claim 1, wherein in the spraying step, the organic solvent or the oil-phase material containing a halogen element is dissolved or dispersed in alcohol or water and sprayed to the surface of the substrate.

4. The foreign material detecting method of claim 1, wherein in the condensing step, the substrate surface is cooled to about 0° C. to about 30° C.

5. The foreign material detecting method of claim 1, wherein the spraying step and the condensing step are performed under the depressurized atmosphere.

6. The foreign material detecting method of claim 1, wherein the organic solvent or the oil-phase material containing a halogen element contains at least one of F, Cl and Br.

7. The foreign material detecting method of claim 6, wherein the oil-phase material containing a halogen element is selected from at least one of hydrofluoroether, hydrochlorofluorocarbon, hydrofluorocarbon, perfluorocarbon and perfluoropolyether.

8. A foreign material detecting apparatus for detecting a foreign material attached to a surface of a substrate, the apparatus comprising:
   a surface processing device having an accommodation chamber for accommodating the substrate, for preprocessing the surface of the substrate; and
   a surface inspecting device for inspecting the preprocessed surface of the substrate, wherein the surface processing device includes:

a spraying unit for spraying an organic solvent or an oil-phase material containing a halogen element to the surface of the substrate; and a temperature control unit for condensing the sprayed organic solvent or oil-phase material around the foreign material attached to the surface of the substrate by controlling a temperature of the surface of the substrate, and wherein the surface inspecting device includes:

a surface inspecting unit for inspecting the surface of the substrate; and a heating unit for heating the foreign material on the substrate, wherein the temperature control unit is configured to remove the condensed organic solvent or the condensed oil-phase material by heating the surface of the substrate such that the substrate is restored to a state where only the foreign material is attached on the substrate.

9. A non-transitory computer readable storage medium storing therein a program for causing a computer to perform a foreign material detecting method for detecting a foreign material attached to a surface of a substrate, wherein the foreign material detecting method includes:

a spraying step of spraying an organic solvent or an oil-phase material containing a halogen element to the substrate surface;

a condensing step of emphasizing the foreign material by condensing the sprayed organic solvent or oil-phase material around the foreign material attached to the substrate surface by controlling a temperature of the substrate surface;

a surface inspecting step of detecting the foreign material emphasized by the condensation of the organic solvent or the oil-phase material by a surface inspecting device, and a restoring step of scattering the condensed organic solvent or the condensed oil-phase material by heating the substrate surface after the surface inspecting step, wherein in the restoring step, the substrate is restored such that only the foreign material is attached thereon while the condensed organic solvent or the condensed oil-phase material is removed.

* * * * *